United States Patent [19]
Sever, Jr.

[11] Patent Number: 5,817,045
[45] Date of Patent: Oct. 6, 1998

[54] APPARATUS AND METHOD FOR ENABLING EXTRACORPOREAL THERAPY OF UP TO AT LEAST ONE HALF OF A LIVING PATIENT'S ENTIRE CIRCULATING BLOOD SUPPLY DURING A CONTINUOUS TIME INTERVAL

[76] Inventor: Frank Sever, Jr., POB 7442, Arlington, Va. 22207

[21] Appl. No.: 818,933

[22] Filed: Mar. 17, 1997

Related U.S. Application Data

[63] Continuation-in-part of Ser. No. 437,311, May 9, 1995, abandoned, which is a continuation-in-part of Ser. No. 427,277, Apr. 24, 1995, abandoned.

[51] Int. Cl.$^6$ .................................................. A61M 37/00
[52] U.S. Cl. ................................. 604/4; 604/5; 128/898; 514/832; 422/44
[58] Field of Search ............................... 604/4–6, 48, 49, 604/52; 128/898; 514/832, 833; 210/766, 645; 422/44–46

[56] References Cited

U.S. PATENT DOCUMENTS

| | | | |
|---|---|---|---|
| 4,464,166 | 8/1984 | Edelson .......................................... | 604/6 |
| 4,824,432 | 4/1989 | Skurkovich et al. ......................... | 604/4 |
| 4,865,841 | 9/1989 | Balint et al. . | |
| 4,878,891 | 11/1989 | Judy et al. .................................... | 604/5 |
| 5,074,838 | 12/1991 | Kroyer . | |
| 5,080,645 | 1/1992 | Hanig . | |
| 5,217,618 | 6/1993 | Murakoshi .................................. | 604/5 |
| 5,514,536 | 5/1996 | Taylor ......................................... | 604/4 |
| 5,536,412 | 7/1996 | Ash .............................................. | 604/5 |
| 5,574,019 | 11/1996 | Segall et al. ................................. | 604/4 |

OTHER PUBLICATIONS

CBS, 60 Minutes, Apr. 2, 1995, 7:00–8:00 PM, "Welcome Back Mrs. Khadder".
*Cryogenics*, McClintock, Reinhold Pub Co, pp. 1–3.
*Cryogenic Engineering*, Bell, Prentice–Hall, Inc, pp. 1–5.

*Primary Examiner*—Mark O. Polutta

[57] ABSTRACT

The instant invention teaches an apparatus and a method for using an apparatus for extracorporeal therapeutic treatment of a changing volume of up to at least about half of the circulating blood of a living patient at one time. The apparatus includes first structure defining a cooling process loop for providing a cooling mode for lowering a patient's body to a hypothermic state; second structure defining a draining process loop for providing a draining mode for draining up to at least about half of the patient's circulating blood supply from the patient while the body of the patient is at about a hypothermic state; third structure defining an extracorporeal therapeutic treatment process loop for providing a extracorporeal therapeutic treatment mode for extracorporeally therapeutically treating the up to at least about half of the patient's entire circulating blood supply; fourth structure defining a re-transfusion process loop for providing a re-transfusion mode for re-transfusing the up to at least about half of the patient's entire circulating blood supply which has been extracorporeally therapeutically treated; fifth structure defining an energy addition process loop for adding energy to raise the temperature of the patient's blood sufficient to stabilize the life signs of the patient; and, sixth structure for sequencing the operation of the first, second, third, fourth and fifth structure, sufficient to cause substantially only the first structure to operate at a first period of predetermined time; then after the first period, to cause substantially only the second structure to operate for a second period of predetermined time; then after the second period, to cause substantially only the third structure to operate for a third period of predetermined time; then after the third period, to cause substantially only the fourth structure to operate for a fourth period of predetermined time; then after the fourth period, to cause substantially only the fifth structure to operate for a fifth period of predetermined time; and, then after the fifth period, to cause substantially only the fifth structure to operate for a fifth period of predetermined time.

9 Claims, 5 Drawing Sheets

APPARATUS AND METHOD FOR ENABLING EXTRACORPOREAL THERAPY OF UP TO AT LEAST ONE HALF OF A LIVING PATIENT'S ENTIRE CIRCULATING BLOOD SUPPLY DURING A CONTINUOUS TIME INTERVAL

RELATED APPLICATION DATA

This is a continuation-in-part of application Ser. No. 08/437,311, filed May 9, 1995, now abandoned which is a continuation-in-part of application Ser. No. 08/427,277, filed Apr. 24, 1995, now abandoned.

BACKGROUND OF THE INVENTION

The instant invention relates to a method and apparatus for enabling withdrawal, extracorporeal therapeutic treatment and recycle back into the body of, up to at least half of all of the internal circulating blood supply of a living patient during a continuous time interval. The invention has special application to a patient whose blood is contaminated by substantially any one or combination of blood born harmful foreign agents such as viruses, organic toxins, inorganic toxins, parasites, pathogens, bacteria, and the like. The instant invention also contemplates treatment of the internal blood wetted surfaces of the patient's blood circulatory system during and within the aforementioned single continuous time interval between when up to at least half of the entire circulating blood supply is substantially entirely withdrawn from the patient and when it is substantially entirely transfused back into the patient. Although the invention in its broadest sense contemplates its application to substantially any living animal having that which can be characterized as "blood," for purposes of illustration only, the disclosure herein will be directed to mammalian animals; particularly to human patients; and even more particularly, to human patients whose blood has been contaminated by the HIV virus.

The Prior Art

Extracorporeal therapy of a minor "detour" or recycle stream of a patient's circulating blood, is well known in the art.

For instance, U.S. Pat. No. 5,074,838, to Kroyer, which is incorporated herein by reference, teaches an extracorporeal thermo therapy device having inlets and outlets which, when connected in shunt to a human patient, provide the blood of the patient with a detour outside of the patient's body. The detour thereby becomes an integral part of the patient's blood circulatory system. Kroyer employs his invention to induce an extracorporeal "fever" in the detour stream to a temperature of about 2° C. above normal body temperature, thus activating the patient's immune system by stimulating the production of white blood cells and anti-bodies. In this manner, the device is claimed to act as an attenuater for destroying the virus. Thus Kroyer shows extracorporeal therapeutic thermal energy treatment of a minor detour blood stream.

Although Kroyer discloses a temperature elevation of merely about 2° C., the instant invention contemplates elevating the blood temperature to as high as possible without damage to the patient's blood. In this manner instant invention contemplates a more complete fragmentation of i.e., virus particles, sufficient to provide novel species of anti-bodies.

In another similar invention, U.S. Pat. No. 4,464,166, to Edelson, incorporated herein by reference, a method and system is disclosed for externally treating human blood to reduce the functioning lymphocyte population in the blood circulatory system of a human patient. Edelson passes an extracorporeal blood detour stream in which he has dissolved about One (1) nanogram to about One hundred (100) micrograms of a photo active agent which coacts with certain cites on an infected cell such as lymphocytic-DNA, mobile cortisone receptors or antigen cites so as to form co-valent bonds between the molecules of the agent and each respective cite thus producing photo-adducts. When these adducts are irradiated with UV energy having a wavelength range of about Two thousand (2000) to about Four thousand (4000) angstroms the metabolic functions of the cell are inhibited and the cell dies. Thus Edelson shows combined extracorporeal chemo/wave energy therapeutic treatment of a minor blood detour stream.

Other conventional methods for extracorporeally, therapeutically treating a blood detour stream, such as those of Kroyer and Edelson, have long been known in the art. Some of these involve various methods of blood fractionation. As disclosed in the Encyclopedia of Human Biology, Volume I, pp 401–405, Academic Press, Inc., San Diego, Calif. (1991), such methods include but are not necessarily limited to: cascade membrane plasmapheresis, hemodialysis, hemoperfusion, membrane plasmapheresis, peritoneal dialysis, single-needle dialysis, hemosoption, hemoperfusion, regular peritoneal dialysis, recirculating peritoneal dialysis, continuous ambulatory peritoneal dialysis (CAPD), and the like. Although there is a plethora of prior art inventions which operate only to therapeutically treat an extracorporeal detour or recycle stream, which constitutes a very minor fraction of the patient's total internal blood capacity, there has hitherto been no method or apparatus designed specifically for the extracorporeal therapeutic treatment of up to at least half of a living patient's entire internal circulating blood supply during a single, uninterrupted time interval.

Hypothermic conditions have been shown to have application in the medical art.

On Apr. 2, 1995, between the hours of 7:00–8:00 PM EST, the CBS Network television program "60 Minutes," aired a story entitled "Welcome back Mrs. Khadder," which is incorporated herein in its entirety, by reference. The story disclosed a radical medical technique, long known, but until then rarely publicized. The subject of the story was Mrs. Maureen Khadder. When she went to her doctor complaining of headaches, she returned home with what amounted to a death sentence. Her doctor told her that she had an aneurysm, or swollen artery, in her brain. If it were to rupture, as it was prone to do, she would die. The risk of conventional brain surgery was tantamount to a death sentence. However, on Jan. 11, 1995, Mrs. Khadder was to undergo a surgical procedure at New York's Columbia Presbyterian Hospital, which would, for a brief period of time, deprive her of all visible signs of life. A team of physicians which included, cardiac surgeon, Dr. Craig Smith, Dr. Robert Solomon, brain surgeon, and anesthesiologist, Dr. Shari Hall, deflated the aneurysm, by draining the blood out of it. To do that, however, they had to drain up to at least half of the blood out of Mrs. Khadder, under conditions which are as close as modern medicine comes, under common circumstances, to clinical death. The key to the operation, was hypothermia. By diverting Mrs. Khadder's blood into a bypass machine, Dr. Smith and his team were able to cool her blood down to about Thirty five (35)° F., below normal, to a point at which her heart had stopped beating. Prior antidotal reports have taught, that under conditions of extreme cold, that a person who has clinically drowned in icy water; who has been clinically dead for as much as One (1) hour; who shows no signs of heartbeat, breathing, brain waves; could nonetheless be brought back to life, by being warmed. Most amazingly, under normal conditions, the human brain suffers irreparable damage when deprived of oxygen for only about Six (6) minutes. At about the time of 12:04 PM, Mrs. Khadder's heart had stopped beating, under a state of hypothermia. Shortly thereafter, when Mrs. Khadder's brain had reached a temperature of at about Sixty four (64)° F., one of the team turned off the pump which was recirculating the blood through her body. The team thereafter proceeded to drain up to at least half of all of her blood out of her body, and store it until they were ready to transfuse it back into her, after they had operated on the aneurysm. At about 12:10 PM, Mrs. Khadder, ceased to register any life signs. At about 12:24 PM, the order was given to activate the blood recirculation pump to the body of Mrs. Khadder. After warming the blood for about Thirty (30) minutes, Mrs. Khadder's body reach a temperature of about Seventy seven (77)° F., and her heart beat again. It was later disclosed in the story, that out of Forty (40) patients upon whom Drs. Smith and Solomon performed the foregoing hypothermic procedure, Thirty seven (37) made it through the procedure. At the conclusion of the story, it was disclosed that physicians have been resurrecting patients from the dead, for some time without public recognition. In Siberia, for instance, for more than Three (3) decades, surgeons have been practicing the technique, without the Hi-tech resources of the western world. There, even with their primitive resources, they had been packing their patients in ice; transporting them into a state of limbo; and resurrecting them to life. They have done it thousands of times. . . Thus was provided the date of conception of the instant invention.

It must be noted that the "half" of the patient's blood removed disclosed to the Khadder reference, merely represented only that necessary amount of blood drained from Mrs. Khadder to deflate her aneurysm sufficiently to enable the surgeons to safely operate on it. Therefore, the upper limit of exactly how much blood could theoretically be drained from a living patient under hypothermic conditions has yet to be determined Indeed, until the instant invention, there has been no reason for heath care providers to explore this uncharted area of medicine.

"Scrubbing" of all tissues and organs with blood substitutes under clinical cryogenic conditions is also well known in the art.

U.S. Pat. No. 5,080,645 to Hanig teaches an emergency replacement procedure or method for rapid and drastic reduction of the body burden of AIDS virus residing primarily in the formed elements of the blood which involves the removal of all blood from the patient and replacement with an emulsion of a perfluorocarbon chemical or other blood substitute, several exchanges of blood substitute in order to attempt a "scrubbing" in totality of the AIDS containing blood from all of the tissues and organs served by vascular beds and then replacement of the emulsion of perfluorocarbon chemical or other blood substitute with whole blood of the same type as the patient; and wherein the above replacement procedure is carried out using antiviral agents or other agents currently shown to reduce, mitigate or destroy the AIDS virus during and after the above said replacement procedure. As an option, Hanig further teaches the use of a blood substituted "that is the patient's own blood that has been cell sorted to so as to contain only red blood cells plasma or physiological solution; or the said blood substitute is typed blood cells in plasma or physiological solution" (see column 4, lines 8 to 12 of Hanig).

Until the instant invention, the prior art has not recognized the opportunity provided by the hypothermic state, for the extracorporeal therapeutic treatment of up to at least half of a living patient's blood during a single time period.

SUMMARY OF THE INVENTION

This invention endeavors to provide a new apparatus and method for its use, which could have a profound capacity to provide a great good for humanity. It provides a window of opportunity for: (a) the extracorporeal treatment of up to at least half of a patient's entire blood supply during a single interval of time; and, (b) the direct therapeutic treatment of all blood wetted internal surfaces of a patient's blood circulatory system with that portion of the recycling blood within the patient's body. Preferably, prior to recycling of the blood within the patient's body, a therapeutic component is added to it, which has the capacity to disable and/or enable removal of residual harmful foreign agents from within the patient's body. The invention provides an apparatus and a method for its use, for enabling withdrawal and extracorporeal therapeutic treatment of a continuously changing volume of up to at least half of the substantially entire internal blood supply of a living patient, whose blood contains a harmful foreign agent, during a single continuous time interval.

The instant method in its broadest expression contemplates an apparatus and a process for its use, which combines: (1) a cooling process loop for providing a cooling mode for cooling the blood of a living patient to hypothermic temperatures, and thus reduce the body temperature of the patient to about a hypothermic state; (2) a draining process loop for providing a draining mode for draining a continuously changing volume of up to at least half of the patient's circulating blood supply from the patient while the body of the patient is at about a hypothermic state; (3) a therapeutic treatment process loop for providing a extracorporeal therapeutic treatment mode for extracorporeally therapeutically treating the up to at least half of the patient's entire circulating blood supply. Optionally, if it should turn out that substantially all of the circulating blood can be withdrawn from a living patient whose body has been reduced to about a hypothermic state, then the instant invention contemplates an additional step, i.e., (3a) (not shown) of recycling blood substitutes comprising concentrations of therapeutic agents through the patient's through the patient's body, while the substantial entirety of the patient's blood is being extracorporeally therapeutically treated pursuant to following step (d); (4) a re-transfusion process loop for providing a re-transfusion mode for re-transfusing the up to at least half of the patient's entire circulating blood supply which has been extracorporeally therapeutically treated; and, (5) an energy addition process loop for adding energy to raise the temperature of the patient's blood sufficient to stabilize the life signs of the patient.

Although the invention has special application to a patient whose blood is contaminated by substantially any one or combination of blood born harmful foreign agents such as viruses, organic toxins, inorganic toxins, parasites, pathogens, and the like, it has particular application to the HIV virus. As noted above the invention also contemplates treatment of the internal blood wetted surfaces of the patient's blood circulatory system during and within the aforementioned single continuous time interval. Although the invention in its broadest sense contemplates its application to substantially any living animal having that which can be characterized as "blood," the disclosure herein will be directed to mammalian animals; particularly to human patients; and even more particularly, to human patients whose blood has been contaminated by the HIV virus.

More specifically, the invention provides a method for extracorporeally therapeutically treating a patient whose blood and body contains substantially any harmful foreign agents, including, but not necessarily limited to: viruses, pathogens, viruses, harmful living organic agents, harmful non-living organic agents, harmful inorganic agents, plaques, parasites, microbes and any combination of the foregoing. A method is provided which includes: cooling the body temperature of a patient to a temperature characteristic of a substantial state of hypothermia. As shown by the foregoing reference to Mrs. Khadder, this state provides a medical opportunity whereby up to at least half of the substantially entire blood supply may be drained from a patient's body. More surprising, up to at least half of the entire supply can be placed in extracorporeal storage for a substantial period; transfused back into the patient; and warmed until the patient again exhibits normal life signs. After cooling to the hypothermic state, a continuously changing volume of up to at least half of substantially all the patient's blood supply may be withdrawn for a substantial time interval, before which re-transfusion is required to sustain the life of the patient. This time interval provides a window of opportunity, wherein up to at least half of the patient's substantially entire blood supply is available for extracorporeal therapeutic treatment. By extracorporeally therapeutically treating that quantity of the patient's blood (i.e., up to at least half of the patient's entire circulating blood supply) while the remaining quantity of the patient's blood is continuously recycled through the patient's body, it is theoretically possible to treat the patient's substantially entire circulating blood supply as well as all internal wetted surfaces of a patient's internal blood circulatory system, in a finite number of recycle passes.

Although the preferred best mode of therapeutic treatment of the invention is extra corporeally adding energy to the blood of a living patient sufficient to induce an extracorporeal fever therein, in a manner similar to that taught by Koyer, supra, it should be understood that the instant invention is by no means intended to be limited thereby. Thus, the instant extracorporeal therapeutic treatment may include any conventionally known and/or experimental therapeutic blood treatment or combinations thereof which results in rendering the harmful agents harmless to patient during the window of opportunity provided by the hypothermic state of the patient's body.

Although not intended as limiting, a typical application of the invention could involve the addition of chelates to the recycling blood for removal of plaques, and the like from walls of the patient's blood vessels. The chelate laden blood would be recycled for a finite number of recycle passes, and the chelates could be removed, preferably during the refill mode of the instant invention.

It is well known that plaque on the walls of a blood vessel often involve calcification. It is equally well known that the calcium ion has an inverse solubility in water, i.e., solubility decreases as a function of temperature. Since blood is substantially comprised of water, it would follow that the calcium ion would also exhibit an inverse solubility with respect to blood. Therefore, at the instant hypothermic state, the practicioner of the invention could expect substantially increased solubility of the calcium ion. Thus, chelation therapy could be expected to be more efficient at hypthemic temperatures. It should be further noted, that since the a finite number of recycle passes are contempleted by the process of the invention, possible damage to the patient's kidneys by chelate compounds used in this therapy, are minimized. Moreover, to completely eliminate risk of damage to the patient's kidneys during the chelation therapy contemplated by the instant invention, the patient's kidneys could be shunted off from the instantly contemplated recycle passes through the patient's body.

BRIEF DESCRIPTION OF THE DRAWINGS

To simplify understanding of the invention, the various process loops have been highlighted in each respective drawings drafted to illustrate it.

DETAILED DESCRIPTION OF THE INVENTION

Figure 1:
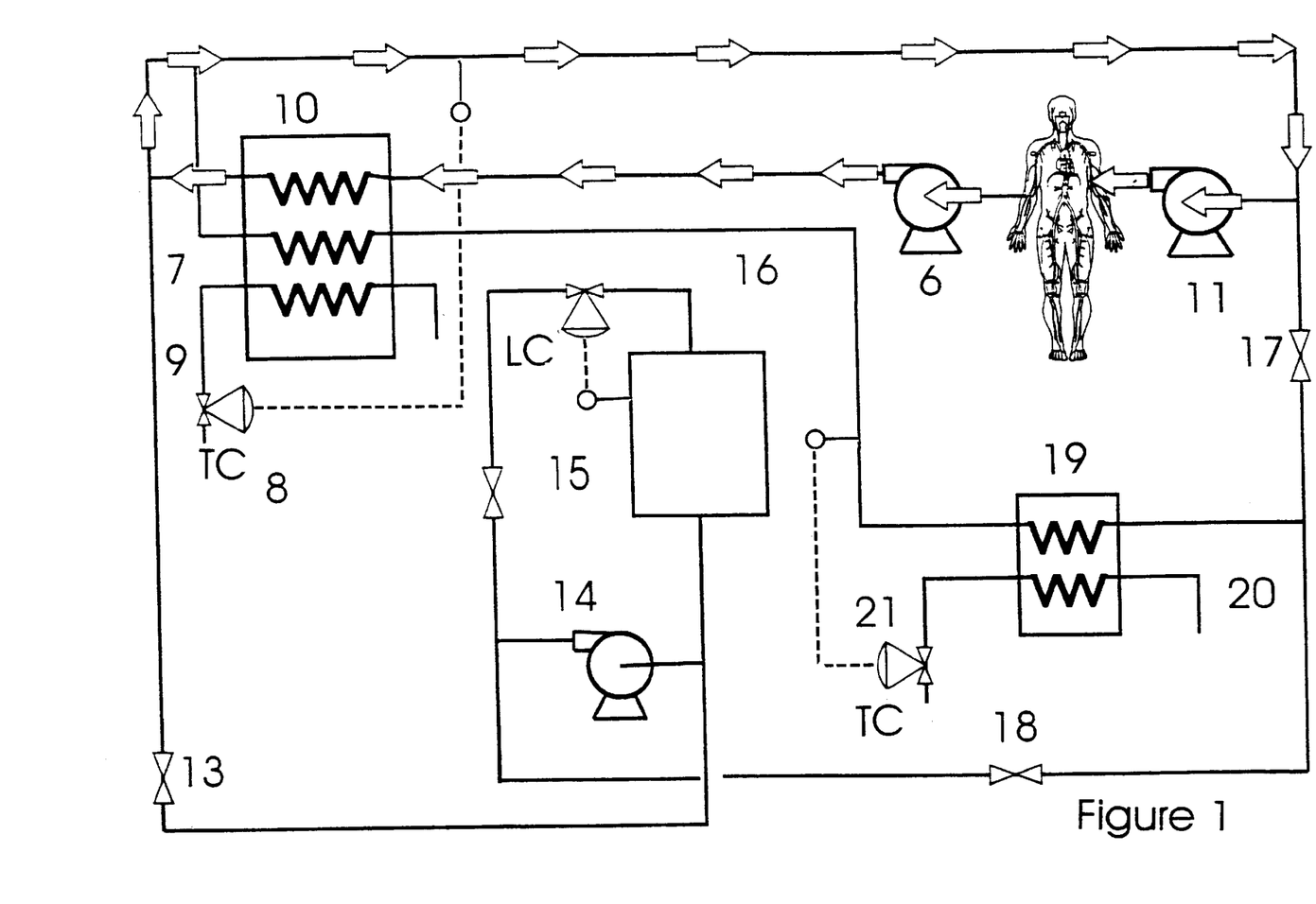
FIG. 1 shows a flow diagram which, for the sake of clarity, depicts a cooling process loop for providing a cooling mode for lowering a patient's body to a hypothermic state (hereinafter referred to as "loop (1)").

As noted above, FIG. 1 shows loop (1) highlighted for the sake of clarity. Loops (2), (3), (4) and (5), have been separately higlighted in the respective FIGS. 2, 3, 4 and 5. Now referring to FIG. 1, blood is withdrawn from, i.e., the right arm of the patient, passed though a pump (6), through heat exchanger (7), where it is cooled by (partially shown) refrigeration cycle (8). Flow through the outlet stream of the refrigeration cycle (8) from heat exchanger (7) is controlled by temperature controller (9) responsive to the temperature of the blood recycle outlet (10) from heat exchanger (7), as the cooled blood is recycled back into the body of the patient through pump (11). Preferably a blood oxygenator (not shown) is provided to oxygenate the blood at some point prior to being re-transfused back into the patient (i.e., between the outlet of pump (11) and the patient).

Figure 2:
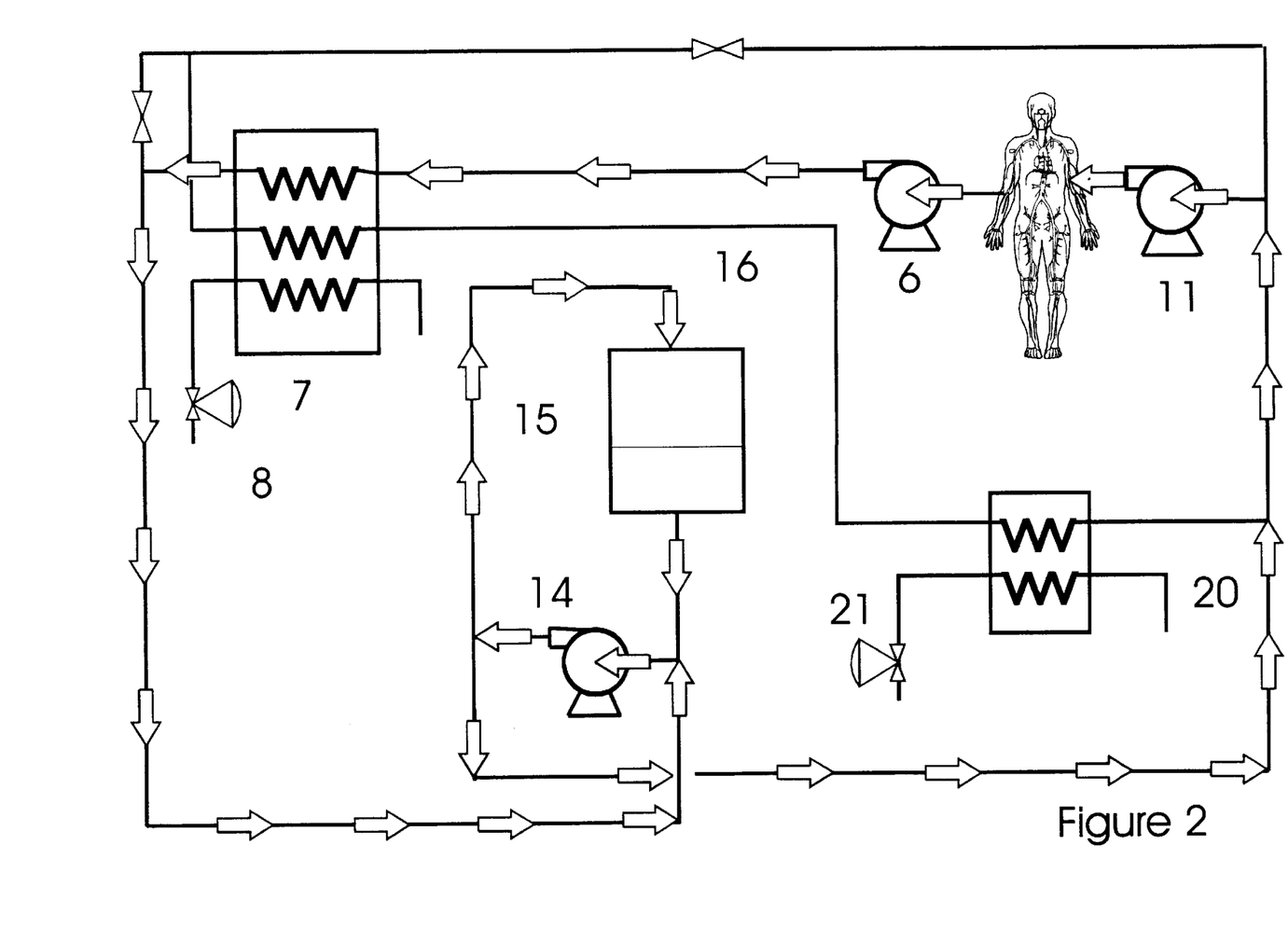
FIG. 2 shows a flow diagram which, for the sake of clarity, depicts loop (1), combined with a draining process loop for providing a draining mode for draining up to at least half of the patient's circulating blood supply from the patient while the body of the patient is at about a hypothermic state (hereinafter referred to as loop "(2)").

FIG. 2, shows loop (1) combined with loop (2), the draining process loop. After the body of the patient is reduced to state of hypothermic temperature, valve (12) is closed and valve (13) (identified only in Figure) is opened (although not shown in FIG. 1, valve (13) would be in the closed state during the cooling mode). The cooled blood is then shunted though pump (14). The outlet stream of pump (14) is then split so that a first portion directed through a recycle line into tank (15) and a second portion is directed through pump (11) back into the patient's body. The flow of the recycle line directing the first portion is controlled by level controller (16) responsive to the level of accumulated cooled blood in tank (15). When up to at least about half of which was formerly the patient's entire circulating blood supply is extracorporeally accumulated in the tank (15) and process lines, the invention is switched to extracorporeal therapeutic treatment mode.

Figure 3:
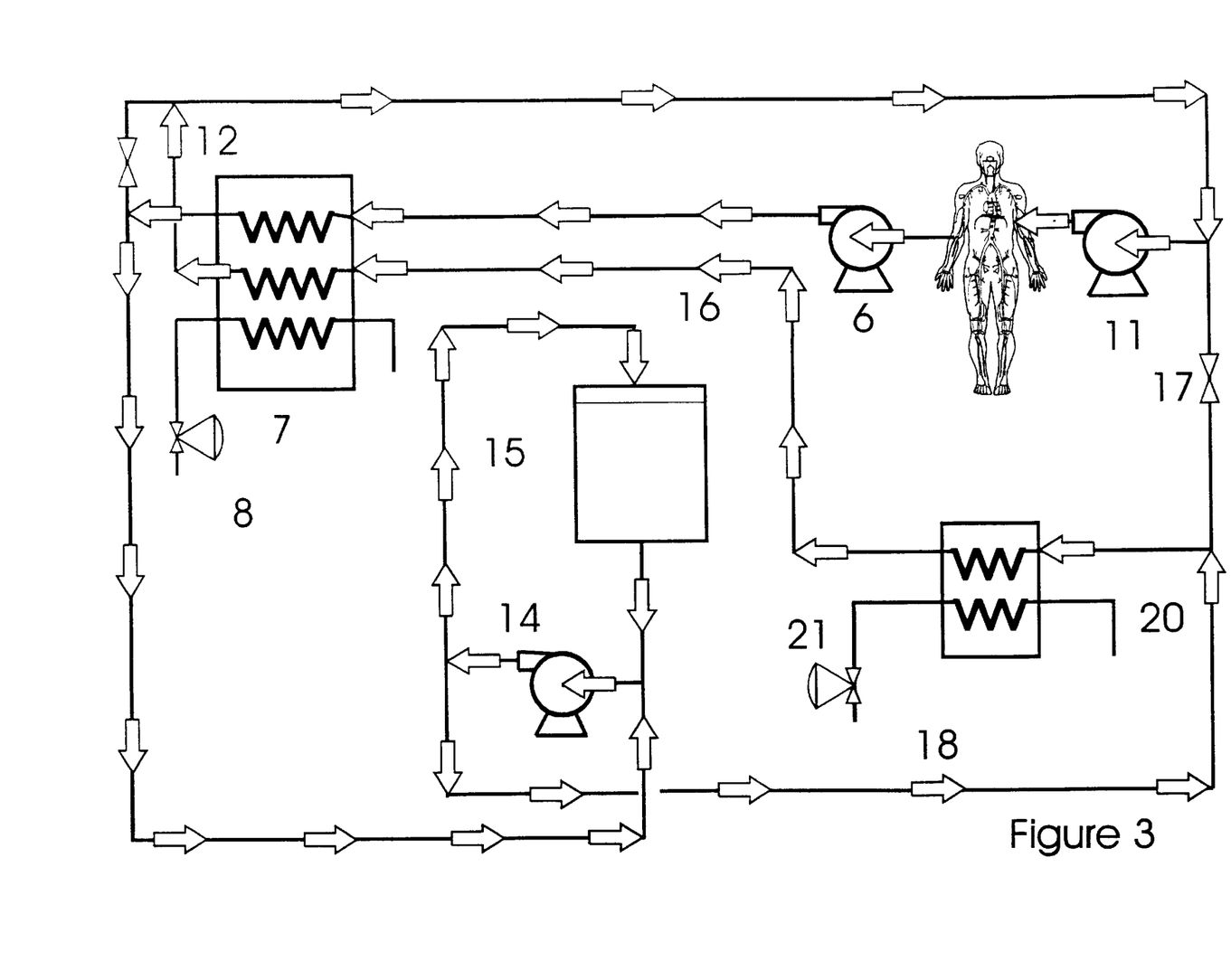
FIG. 3 shows a flow diagram which, for the sake of clarity, depicts loops (1) and (2), further combined with an extracorporeal therapeutic treatment process loop for providing a extracorporeal therapeutic treatment mode for extracorporeally therapeutically treating the up to at least half of the patient's entire circulating blood supply (hereinafter referred to as "loop (3)").

FIG. 3, shows loop (1) combined with loop (2), further combined with the extracorporeal therapeutic treatment mode, loop (3). During this phase of the invention, valve (17) is closed and valve (18) (not shown, and not open, in previous FIGS. 1 and 2) is open, thereby diverting the second portion of pump 14 through heat exchanger (19) where preferably it is heated to induce an extracorporeal fever on the patient's blood sufficient to stimulate the production of white blood cells and anti-bodies in it (similar to the manner taught by Kroyer, but differing in kind from Kroyer), prior to being re-cooled in heat exchanger (7) and thereafter pumped back into the patient through pump 11. The flow through the outlet line of heating loop (20) is controlled by temperature controller (21) in response to the temperature of the blood stream outlet line from heat exchanger (19). The so treated blood is recycled through the body a sufficient number of recycle passes to ensure that the entire circulating contents of the patient's blood circulatory system has been extracorporeally treated. Although heating is the preferred mode of extracorporeal therapeutic treatment, it is by no means intended to limit the invention in any manner since any other mode or combination of modes of conventional extracorporeal therapeutic blood treatment are instantly contemplated. For example, a therapeutic agent such as a drug for treating the internal wetted surfaces of the patient's blood circulatory system, might also be added to the blood stream at some point prior to re-transfusion through pump (11); and removed by some conventional mode or combination of conventional modes, after some predetermined treatment time at some point downstream of pump (6).

Figure 4:
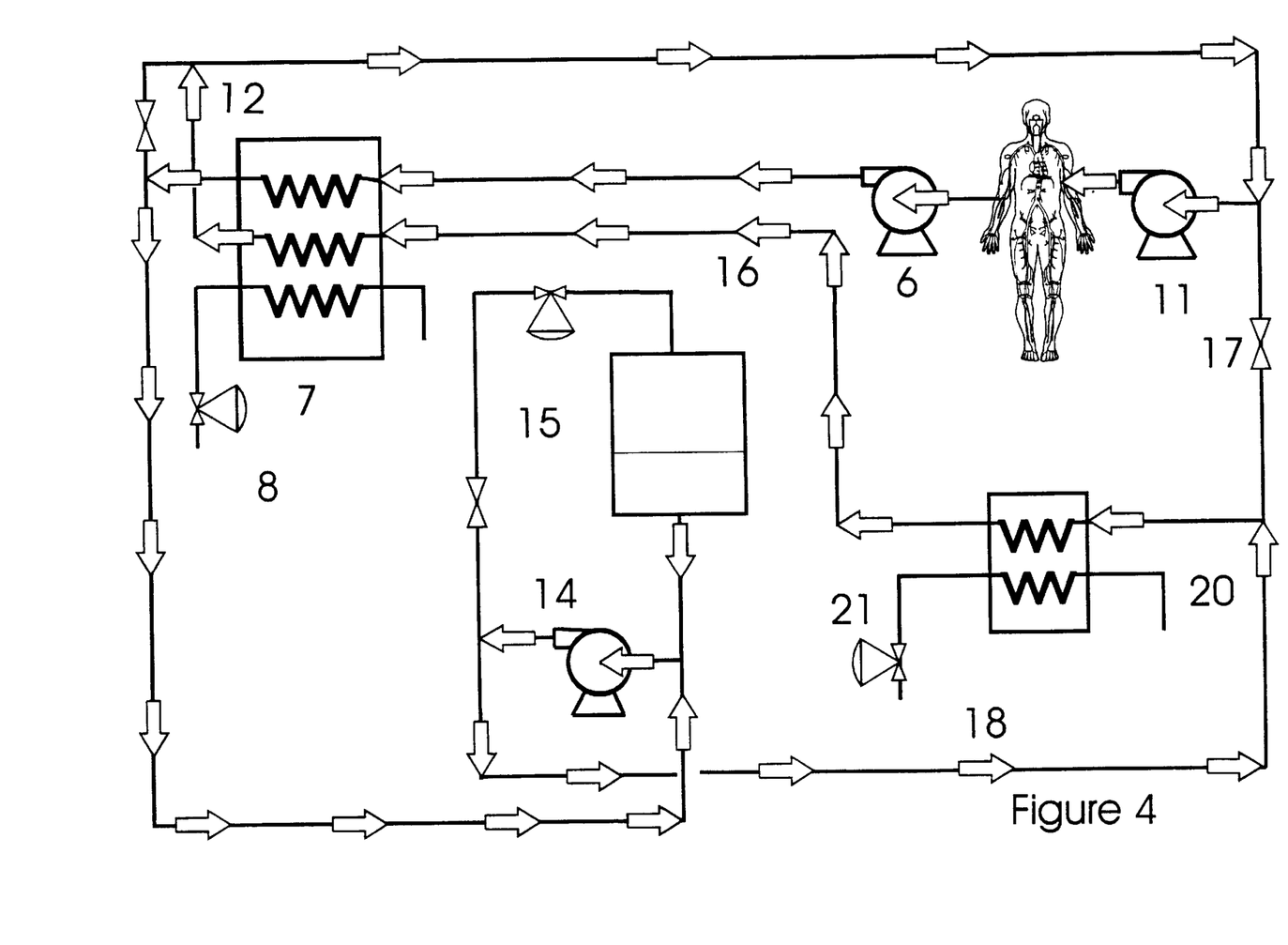
FIG. 4 shows a flow diagram which, for the sake of clarity, depicts loops (1), (2) and (3), further combined with a re-transfusion process loop for providing a re-transfusion mode for re-transfusing the up to at least half of the patient's entire circulating blood supply which has been extracorporeally therapeutically treated (hereinafter referred to as "loop (4)").
Figure 5:
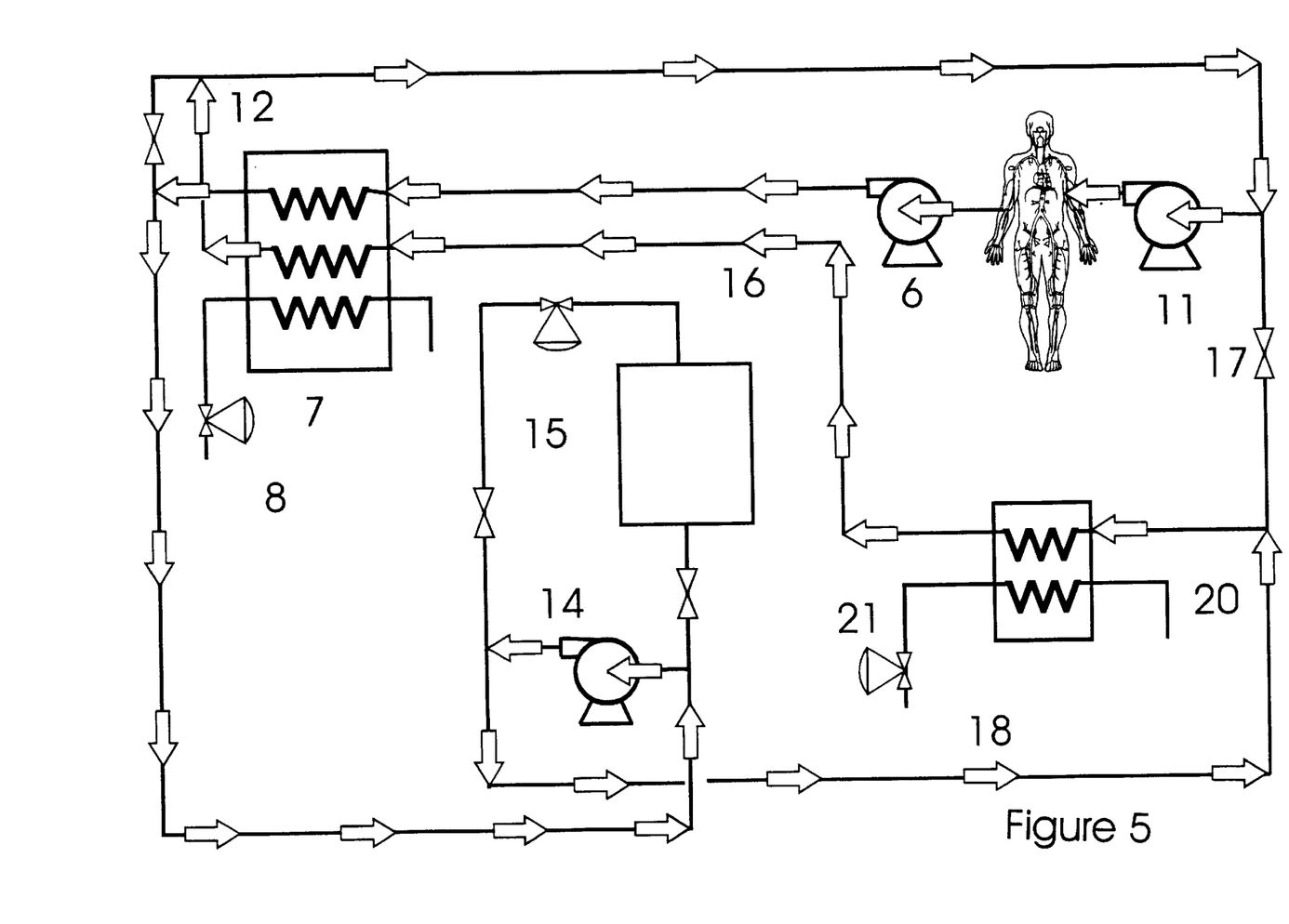
FIG. 5 shows a flow diagram which, for the sake of clarity, depicts loops (1), (2), (3) and (4), further combined with an energy addition process loop for adding energy to raise the temperature of the patient's blood sufficient to stabilize the life signs of the patient (hereinafter referred to as "loop (5)").

FIG. 4 shows loop (1) combined with loop (2), further combined with loop (3), still further combined with the re-transfusion process loop for providing a re-transfusion mode for re-transfusing the up to at least half of the patient's entire circulating blood supply which has been extracorporeally therapeutically treated, loop (4). After a number of recycle passes of the extracorporeally treated blood through the body of the patient, sufficient to ensure that substantially all of the patient's blood and internal wetted surfaces of the patient's blood circulatory system have been therapeutically treated, the invention is switched to blood re-fill mode.

Older, more conventional control schemes have been used in the detailed description merely for the purpose of simplifying explanation of the invention, and is by no means intended to limit the scope of the invention. Thus, although not particularly depicted in the instant drawings, the instant use of microprocessor control is preferred.

It must again be emphasized that the instant extracorporeal therapeutic treatment mode contemplates any one mode from any conventional blood separation mode or any combination thereof. The separation methods contemplated by this alternative of the invention include, but are not necessarily limited to: cascade membrane plasmapheresis, hemodialysis, hemoperfusion, membrane plasmapheresis, peritoneal dialysis, single-needle dialysis, hemosoption, hemoperfusion, regular peritoneal dialysis, recirculating peritoneal dialysis, continuous ambulatory peritoneal dialysis (CAPD), hemoultrafiltration, hemofiltration, blood centrifugation, and the like.

It should also be noted that the term "hypothemic" [or any of its variants], as typically used herein, refers to the lowest temperatures to which a living body can be reduced, while still enabling restoration of the patient to normal body function, upon subsequent warming.

"Finite," as used herein, typically refers to the longest possible period of time.

"Extracorporeal" [or any of its variants], as used herein, refers to outside the body of the patient, as opposed to within the body of the patient.

It must further be understood that the claimed "up to at least about half" of the patient's entire circulating blood supply [or any variant thereof], as used herein refers to that maximum quantity of blood which may be withdrawn, while still enabling subsequent restoration of the patient's body to substantially normal function.

Although sequential operation of the instant modes is preferred, the claimed language ". . . sufficient to cause substantially only said . . . [first to fifth]. . . structure to operate . . . ," is intended to mean that there can be at least some preset operational overlap between the period during which an instant mode and a subsequent instant mode are in operation, if so desired.

The instant invention also contemplates the use of blood substitutes to make up blood loss.

The blood substitutes which are contemplated by the instant invention are well known in the prior art. Exemplary of such blood substitutes are those disclosed by the following authority: Author-International Society for Artificial Cells and Immobilization Biotechnology, Title-Artificial Cells, Blood Substitutes, and Immobilization Biotechnology, Vol. 22, no. 1-, Publisher-M. Dekker, 1994, National Library of Medicine (hereinafter, referred to as "NLM") Call Number W1 AR955G; Author-Thomas Ming Swi Chang, Title-Blood Substitutes and Oxygen Carriers, Publisher-Marcel Dekker, Inc., 1993, NLM Call Number LC Card No. W1 BI852RR v.20 no.2–4, 1993; Author-Eishum E. Tsuchida, Title-Artificial Red Cells: Materials, Performance, and Clinical Study as Blood Substitutes, NLM Call Number (not yet available), NLM UI-9442692, ISBN-0-471-95614-7, Publisher-J. Wiley & Sons, Chichestrer, N.Y., 1992; Author- Robert M. Winslow et al, Title: Blood Substitutes: Physiological Efficacy, Publisher-Birkhauser, Boston, Mass., NLM Call No. (not yet available), NLM UI 9502022, ISBN 0-8176-3804-0; and, Author: Jacqueline Van de Kamp, Title: Blood Substitutes: January 1986 through December 1990: 744 Citations, NLM Call Number ZW 1 N272 no. 90-16.

Antiviral drugs, particularly specific to the HIV virus are also well know in the art. They include all those disclosed in the following authority: Author-Jonathan Kam, Title: HIV: A Practical Approach—1st Ed., Publisher-IRL Press at Oxford University Press, Oxford, N.Y., 1995, NLM UI 9505955; Author-Volker Schafer, Title-Partikulare Arsneistofftrager als System for Drug-Targeting: sur Therapie der HIV-Infektion und AIDS, Publisher-FrankfurtMain: VAS, 1993, NLM Call Number 1994 A-311; Author-Peter K. Kessler, et al, Title-Disulfiram and its Metabolite Diethyldithiocarbamate: Pharmacology and Status in the Treatment of Alcoholism, HIV Infections, AIDS and Heavy Metal Toxicity—1st Ed., NLM Call Number WM 274 G392d 1992; and, Author-Robin Weiss, et al, Roundtable for the Development of Drugs and Vaccines Against AIDS (Institute of Medicine), Title-Surrogate Endpoints in Evaluating the Effects of Drugs Against HIV Infection and AIDS: Sep. 11–12, 1989: Conference Study, Publisher-National Academy Press, Washington, D.C., 1990, NLM Call Number WD 308 R859s 1989.

References to AIDS, are also made at Home Medical Encyclopedia, The American Medical Association, Volume One, Random House, N.Y., 1989, pp 76, et seq., and The Essential Guide to Prescription Drugs, James, W. Long, et al, Harper Perennial, 1994, pp 32, et seq.; references to Viruses at Home Medical Encyclopedia, The American Medical Association, Volume Two, Random House, N.Y., 1989, pp 1050, et seq.; references to Parasite(s) at Home Medical Encyclopedia, The American Medical Association, Volume Two, Random House, N.Y., 1989, pp 770, et seq.; references to Poisoning at Home Medical Encyclopedia, The American Medical Association, Volume Two, Random House, N.Y., 1989, pp 805, et seq.; references to Chemotherapy of Parasitic Diseases, at The Phamachological Basis of Therapeutics, Alfred Goodman Gilman, et al, MacMillan Publishing Company, N.Y., 1985, pp 1066, et seq.; and references to Heavy Metals and Heavy-Metal Antagonists, at The Phamachological Basis of Therapeutics, Alfred Goodman Gilman, et al, MacMillan Publishing Company, N.Y., 1985, pp 1605, et seq.

Although the invention has been described with reference to certain preferred embodiments, in particular the HIV virus, it will be appreciated that many variations and modifications may be made within the scope of the broad principles of the invention. Hence, it is intended that the preferred embodiments and all of such variations and modifications be included within the scope and spirit of the invention, as defined by the following claims.

I claim:

1. An apparatus for extracorporeally treating up to at least about half of the circulating blood of a living patient at a given period of time, comprising:

first structure defining a first process loop for cooling the temperature of the body of said patient to a hypothermic state;

second structure defining a second process loop for draining up to at least about half of the patient's circulating blood supply from the patient at a given period of time, while said body of said patient is at about said hypothermic state;

third structure defining a third process loop for extracorporeally therapeutically treating said up to at least about half of said patient's entire circulating blood supply a given period of time;

fourth structure defining a fourth process loop for re-transfusing up to at least about half of the patient's entire circulating blood supply which has been extracorporeally therapeutically treated back into said patient;

fifth structure defining a fifth process loop for adding energy to raise the temperature of the patient's blood sufficient to stabilize the life signs of the patient; and, sixth structure for sequencing the operation of said first, second, third, fourth and fifth structure, sufficient to cause substantially only said first structure to operate at a first period of predetermined time; then after said first period, to cause substantially only said second structure to operate for a second period of predetermined time; then after said second period, to cause substantially only said third structure to operate for a third period of predetermined time; then after said third period, to cause substantially only said fourth structure to operate for a fourth period of predetermined time; then after said fourth period, to cause substantially only said fifth structure to operate for a fifth period of predetermined time; and, then after said fifth period, to cause substantially only said fifth structure to operate for a fifth period of predetermined time.

2. The apparatus of claim 1, wherein:

said first process loop comprises in sequential communication: a first pump; a refrigerating heat exchanger having a first and second process side; a conduit for communicating the discharge port of said first pump to the first process side inlet of said refrigerating heat exchanger; a second pump; a conduit for communicating the first process side outlet of said refrigerating heat exchanger with the suction port of said second pump;

said second process loop further comprises, in sequential communication: said first pump, said conduit for communicating the discharge port of said first pump to the first process side inlet of said refrigerating heat exchanger; a third pump having a discharge with a first and second branch; a conduit for communicating the first process side outlet of said refrigerating heat exchanger with the suction port of said third pump; a tank; a conduit for communicating said first branch with the an inlet of said tank and a conduit for communication an outlet of said tank with the suction port of said third pump; a conduit for communicating said second branch with the suction port of said second pump;

said third process loop further comprises in sequential communication: said first pump; said refrigerating heat exchanger; a conduit for communicating the discharge port of said first pump with the first process side inlet of said refrigerating heat exchanger; said third pump having said discharge with said first and said second branch; a conduit for communicating the first process side outlet of said refrigerating heat exchanger with the suction port of said third pump; said tank; a conduit for communicating said first branch with the an inlet of said tank and a conduit for communicating an outlet of said tank with the suction port of said third pump; a heating heat exchanger; a conduit for communicating said second branch with the process side inlet of said heating heat exchanger; said refrigerating heat exchanger; a conduit for communicating the process side outlet of said heating heat exchanger with a second process inlet of said refrigerating heat exchanger; said second pump; a conduit to communicating the second process outlet of said refrigerating heat exchanger with the suction port of said second pump;

said fourth process loop further comprises in sequential communication: said first pump; said refrigerating heat exchanger; a conduit for communicating the discharge port of said first pump with the first process side inlet of said refrigerating heat exchanger; said third pump; said tank; a conduit for communicating an outlet of said tank with the suction port of said third pump; said heating heat exchanger; a conduit for communicating the discharge port of said third pump with the process side inlet of said heating heat exchanger; said refrigerating heat exchanger; a conduit for communicating the process side outlet of said heating heat exchanger with the second process side inlet of said refrigerating heat exchanger; said second pump; a conduit for communicating the second process side outlet with the suction port of said second pump; and, said fifth process loop further comprises, in sequential communication: said first pump; said refrigerating heat exchanger; a conduit for communicating the discharge port of said first pump with the first process side inlet of said refrigerating heat exchanger; said third pump; said heating heat exchanger; a conduit for communicating the discharge port of said third pump with the process side inlet of said heating heat exchanger; said refrigerating heat exchanger; a conduit for communicating the process side outlet of said heating heat exchanger with the second process side inlet of said refrigerating heat exchanger; said second pump; a conduit for communicating the second process side outlet with the suction port of said second pump.

3. The apparatus of claim 1, wherein said sixth structure comprises a microprocessor.

4. The apparatus of claim 1, wherein said extracorporeal therapeutic treatment mode comprises a conventional blood therapeutic treatment mode or any combination of conventional blood therapeutic treatment modes.

5. The apparatus of claim 2, wherein said first branch comprises a level controller for controlling the flow in said first branch in response to the cooled blood level in said tank.

6. The apparatus of claim 2, wherein said heating heat exchanger comprises a temperature controller for controlling the flow rate of the outlet of the heating side of said heating heat exchanger in response to the temperature of the outlet of the process side of said heating heat exchanger.

7. The apparatus of claim 2, wherein said refrigerating heat exchanger comprises a temperature controller for controlling the flow rate of the outlet of the cooling side of said refrigerating heat exchanger and of the outlet of the cooling coil of the refrigerating loop of said tank are in response to the temperature of the outlet of said second process side of said refrigerating heat exchanger.

8. An apparatus for extracorporeally treating up to at least about half of the circulating blood of a living patient at one time, comprising:

first structure for lowering the temperature of a patient's body to a hypothermic state;

second structure for draining up to at least about half of the patient's circulating blood supply from the patient while the body of the patient is at about a hypothermic state;

third structure for extracorporeally therapeutically treating the up to at least about half of the patient's entire circulating blood supply; and, fourth structure for re-transfusing the up to at least about half of the patient's entire circulating blood supply which has been extracorporeally therapeutically treated;

fifth structure for adding energy to raise the temperature of the patient's blood sufficient to stabilize the life signs of said patient;

sixth structure for sequencing the operation of said first, second, third, fourth and fifth structure, sufficient to cause substantially only said first structure to operate at a first period of predetermined time; then after said first period, to cause substantially only said second structure to operate for a second period of predetermined time; then after said second period, to cause substantially only said third structure to operate for a third period of predetermined time; then after said third period, to cause substantially only said fourth structure to operate for a fourth period of predetermined time; then after said fourth period, to cause substantially only said fifth structure to operate for a fifth period of predetermined time; and, then after said fifth period, to cause substantially only said fifth structure to operate for a fifth period of predetermined time.

9. A process comprising:

providing an apparatus for extracorporeally treating up to at least about half of the circulating blood of a living patient at one time, which includes:

first structure for lowering the temperature of a patient's body to a hypothermic state;

second structure for draining up to at least about half of the patient's circulating blood supply from the patient while the body of the patient is at about a hypothermic state;

third structure defining an extracorporeal therapeutic treatment process loop for extracorporeally therapeutically treating the up to at least about half of the patient's entire circulating blood supply; and, fourth structure defining a re-transfusion process loop for re-transfusing the up to at least about half of the patient's entire circulating blood supply which has been extracorporeally therapeutically treated;

fifth structure for adding energy to raise the temperature of the patient's blood sufficient to stabilize the life signs of said patient;

sixth structure for sequencing the operation of said first, second, third, fourth and fifth structure, sufficient to cause substantially only said first structure to operate at a first period of predetermined time; then after said first period, to cause substantially only said second structure to operate for a second period of predetermined time; then after said second period, to cause substantially only said third structure to operate for a third period of predetermined time; then after said third period, to cause substantially only said fourth structure to operate for a fourth period of predetermined time; then after said fourth period, to cause substantially only said fifth structure to operate for a fifth period of predetermined time; and, then after said fifth period, to cause substantially only said fifth structure to operate for a fifth period of predetermined time;

wherein said first, second, third, fourth and fifth loop, each share a common inlet and outlet;

communicating said inlet with a first point of the blood circulatory system of said patient;

communicating said outlet with a second point of said blood circulatory system, selected relative to said first point, to ensure substantially complete recycle through the body of said patient when said apparatus is in operation; and, operating said apparatus.

* * * * *